United States Patent
Ferrelli et al.

(10) Patent No.: US 11,940,266 B2
(45) Date of Patent: Mar. 26, 2024

(54) PROCESS FOR RAPIDLY MEASURING COEFFICIENT OF MOISTURE EXPANSION (CME) VALUES FOR MATERIALS

(71) Applicant: The Aerospace Corporation, El Segundo, CA (US)

(72) Inventors: Geena L. Ferrelli, Marina Del Rey, CA (US); Hyun I. Kim, Brea, CA (US); Rafael J. Zaldivar, Redondo Beach, CA (US)

(73) Assignee: THE AEROSPACE CORPORATION, El Segundo, CA (US)

( * ) Notice: Subject to any disclaimer, the term of this patent is extended or adjusted under 35 U.S.C. 154(b) by 50 days.

(21) Appl. No.: 17/481,184

(22) Filed: Sep. 21, 2021

(65) Prior Publication Data
US 2023/0091655 A1    Mar. 23, 2023

(51) Int. Cl.
*G01B 11/24*    (2006.01)
*G01N 21/84*    (2006.01)
(Continued)

(52) U.S. Cl.
CPC ......... *G01B 11/24* (2013.01); *G01N 21/8422* (2013.01); *G06T 7/001* (2013.01); *G06T 7/64* (2017.01)

(58) Field of Classification Search
CPC ......... G01B 11/24; G01B 11/00; G01B 11/02; G01B 11/028; G01B 11/16; G01B 11/161;
(Continued)

(56) References Cited

U.S. PATENT DOCUMENTS 5,251,476 A * 10/1993 Gilmore ................. G01N 5/045
374/14
5,685,192 A * 11/1997 Shriner .................. G01G 19/00
73/865.6
(Continued)

OTHER PUBLICATIONS

Zaldivar, Rafael & Ferrelli, Geena & Kim, Hyun. (2019). Underlying causes of hygroscopic stability in high-quality replicated composite optics Proceedings of SPIE vol. 10998, 1099809 (2019). (Year: 2019).*

(Continued)

*Primary Examiner* — Daniel R Miller
*Assistant Examiner* — Eric Sebastian Von Wald
(74) *Attorney, Agent, or Firm* — LeonardPatel PC

(57) ABSTRACT

Processes for rapidly and accurately measuring the coefficient of moisture expansion for materials, such as adhesives, are disclosed. A replication technique may be used to manufacture highly flat and smooth adhesive samples. Moisture is introduced in a controlled humidity atmosphere, distortion is monitored with an accurate laser interferometer (e.g., ~1 nanometer (nm) accuracy), and measurements are correlated with moisture content change. Such processes decrease sample size by three orders of magnitude as compared with conventional techniques and have a smaller adhesive mass requirement, which enables measurement of expensive microelectronic adhesives that were previously cost-prohibitive to measure. Also, thinner films allow CME measurements of ultraviolet (UV) cured adhesives that would otherwise have depth of penetration issues. Furthermore, saturation occurs quickly, allowing pre-stabilization at room temperature, which enabled parametric studies as a function of processing or cure state. Additionally, testing occurs within hours versus months, enabling short lead times for root-cause investigations.

24 Claims, 17 Drawing Sheets

(51) Int. Cl.
*G06T 7/00* (2017.01)
*G06T 7/64* (2017.01)

(58) Field of Classification Search
CPC . G01B 11/2441; G11B 7/2533; G11B 7/2537; G06T 7/64; G06T 7/60; G06T 7/62; G06T 7/0002; G06T 7/0004; G06T 7/001; G01N 21/8422; G01N 2021/8427; G01N 21/453; G01N 2223/613; G01N 5/02; G01N 5/025; G01N 21/3554; G01N 2201/0238; G01N 27/121; G01N 2291/0256; G01N 2291/02809; G01N 2223/607; G01N 2001/364; Y10T 428/287
See application file for complete search history.

(56) References Cited

U.S. PATENT DOCUMENTS

| | | | |
|---|---|---|---|
| 10,562,209 B2 | 2/2020 | Kim et al. | |
| 2007/0214467 A1* | 9/2007 | Fukuda | G11B 7/2403 |
| 2010/0121607 A1* | 5/2010 | Nabatova-Gabain | G01B 11/065 702/172 |
| 2016/0290789 A1* | 10/2016 | Smith | G01B 11/2441 |

OTHER PUBLICATIONS

Hsu, Hsiang-Chen & Hsu, Yu-Teng & Hsich, Wen-Lo & Weng, Meng-Chieh & ZhangJian, Shao-Tang & Hsu, Feng-Jui & Chen, Yi-Feng & Fu, Shen-Li. (2008). Hygroscopic Swelling Effect on Polymeric Materials and Thermo-hygro-mechanical Design on Finger Printer Package. 291-294. 10.1109/IMPACT.2008.4783868. (Year: 2008).*

Zaldivar, Rafael & Kim, Hyun & Ferrelli, Geena. (2017). Hygroscopic and thermal stability of high precision replicated epoxy composite mirrors. Optical Engineering. 56. 1. 10.1117/1.OE.56.11.117103. (Year: 2017).*

G. Ferrelli, H. Kim, and R. Zaldivar, "Effect of photoinitiator concentration on hygroscopic stability of UV cured precision replicated composite optics," Appl. Opt. 59, 4606-4617 (2020). (Year: 2020).*

Zaldivar, Rafael & Kim, Hyun & Ferrelli, Geena. (2018). Effect of gamma radiation on the stability of UV replicated composite mirrors. Optical Engineering. 57. 1. 10.1117/1.OE.57.4.047102. (Year: 2018).*

John D. Strock "Development of Zero Coefficient of Thermal Expansion composite tubes for stable space structures", Proc. SPIE 1690, Design of Optical Instruments, (Sep. 16, 1992); https://doi.org/10.1117/12.137997 (Year: 1992).*

Obeid, H., Clément, A., Fréour, S., Jacquemin, F., & Casari, P. (Mar. 1, 2018a). On the identification of the coefficient of moisture expansion of polyamide-6: Accounting differential swelling strains and plasticization. ScienceDirect. Retrieved Apr. 7, 2023. (Year: 2018).*

* cited by examiner

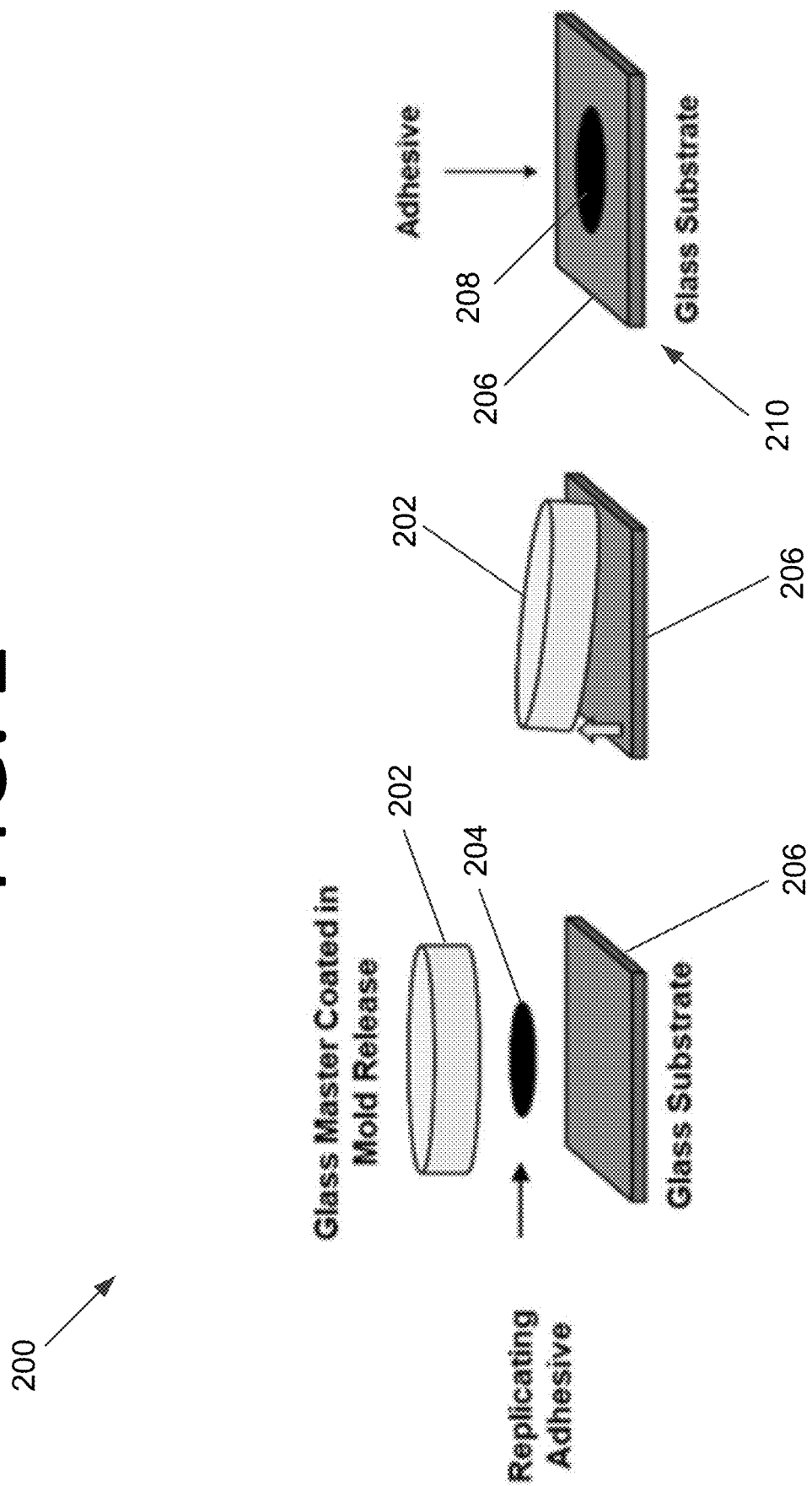

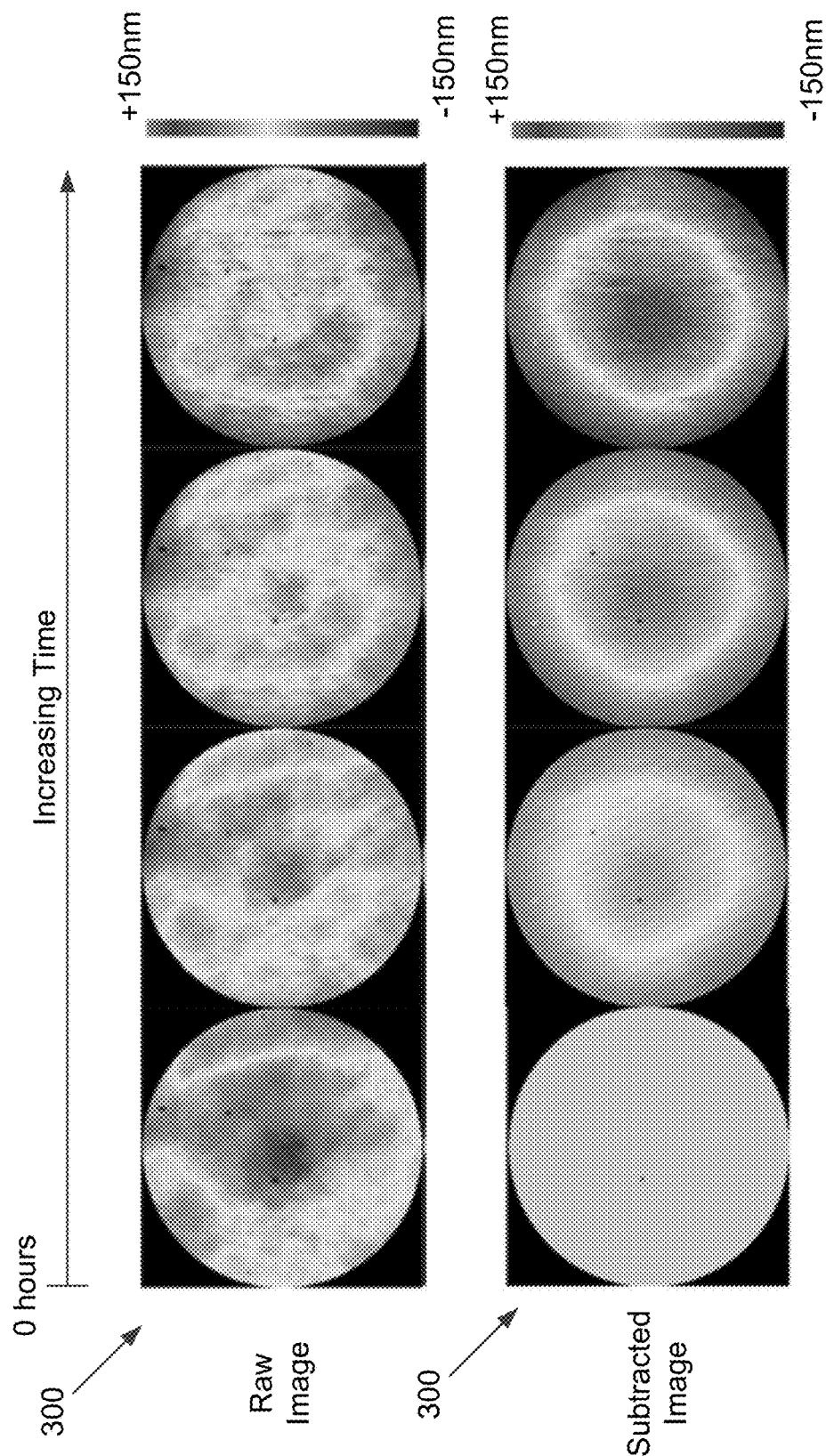

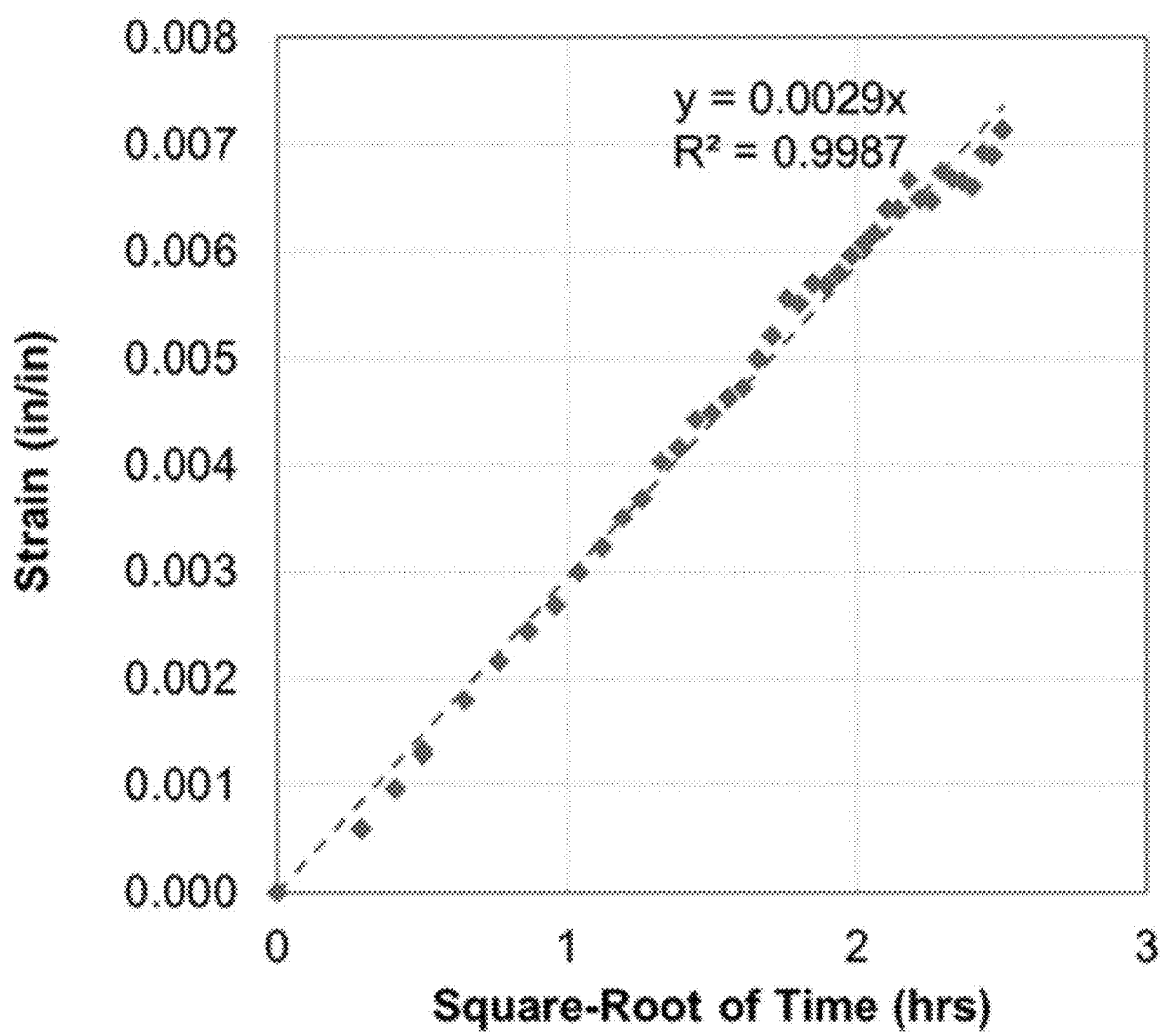

PROCESS FOR RAPIDLY MEASURING COEFFICIENT OF MOISTURE EXPANSION (CME) VALUES FOR MATERIALS

FIELD

The present invention generally pertains to materials analysis, and more particularly, to a process for rapidly measuring coefficient of moisture expansion (CME) values for materials.

BACKGROUND

Polymeric materials can undergo dimensional changes based on the amount of moisture absorption or desorption they undergo in a selected environment. This is especially critical when dealing with organic polymers used as adhesives and/or matrix materials used in composites that may exhibit large dimensional changes once exposed to space environments since a high degree of dimensional stability is often required for aircraft, spacecraft, and high precision electronic components. These dimensional changes can lead not only to distortion and changes in alignment of sensitive optical components, causing misalignment thereof, but can also result in the buildup of large residual stresses, which can cause premature failure of sensitive electronic devices. Compared to the more commonly known coefficient of thermal expansion (CTE), coefficient of moisture expansion (CME) values are typically on the order of 100 times higher and are unavoidable in space-based applications.

The CME is defined as the fractional change in the strain per unit mass variation due to moisture absorption or desorption. The CME is typically determined by measuring the moisture content change and the strain change between the two moisture equilibrium states. CME values are conventionally difficult to measure since specialized equipment and large amounts of time are required. The CME is given by the following:

$$CME = \frac{\Delta l/l_0}{(\Delta m/m_0 [\%])} \quad (1)$$

where $l_0$ is the initial length, $m_0$ is the initial mass, $\Delta l$ is the change in length, and $\Delta m$ is mass variation. The change in length in a hypothetical sample 100 as water is absorbed is shown in FIG. 1.

Typically, these measurements are obtained by using dilatometers utilizing a linear variable displacement transducer (LVDT) or a laser interferometer to correctly monitor changes in dimension with changes in water uptake. Specimens are typically 10 inches in length to minimize error. Specimens also require long stabilization times to fully saturate and desorb the part prior to and during testing. A typical series of tests can take anywhere from 6-8 months to obtain a valid CME value. This process is both costly and time-consuming. In addition, the cure state of the adhesive may be altered during elevated temperature dry-out prior to testing, which significantly affects the behavior of the same materials. Furthermore, manufacturing multiple silver and gold-filled epoxy adhesives utilized using this typic a of configuration is usually cost prohibitive. For instance, such adhesives may cost $1,000 or more for one cubic centimeter. Accordingly, an improved process that can quickly and accurately evaluate how changes in the processing of the material can affect the CME may be beneficial.

SUMMARY

Certain embodiments of the present invention may be implemented and provide solutions to the problems and needs in the art that have not yet been fully solved by existing processes for determining CME values. For example, some embodiments pertain to a process for rapidly measuring coefficient of moisture expansion (CME) values for materials that can provide results orders of magnitude faster than existing techniques. In the process of some embodiments, very thin films of the material are replicated on very thin substrates and a laser is used to measure changes in curvature over time.

In an embodiment, a method for determining CME values for materials includes placing one or more coupons in a gaseous environment with a target relative humidity. The one or more coupons include a flat substrate and a film. The method also includes saturating or drying the one or more coupons in the gaseous environment, measuring changes in curvature of the film over time using a laser interferometer, and measuring changes in mass of the film over time during the saturating or drying. The method further includes converting the changes in curvature in the measurements that occur out-of-plane with a uniform radius of curvature to a strain value. Additionally, the method includes determining the CME using the strain values as a fractional change in the strain value per unit mass variation from the measured changes in mass due to moisture absorption or desorption of the film.

In another embodiment, a method for determining CME values for adhesive materials includes placing one or more coupons in a gaseous environment with a target relative humidity. The one or more coupons include a flat substrate and an adhesive film of an adhesive to be tested. The method also includes saturating or drying the one or more coupons in the gaseous environment, measuring changes in curvature of the adhesive film over time using a laser interferometer, measuring changes in mass of the adhesive film over time during the saturating or drying, converting the changes in curvature in the measurements that occur out-of-plane with a uniform radius of curvature to a strain value, and correlating the measured changes in mass to the strain values as a function of time. The method further includes determining the CME using the strain values as a fractional change in the strain value per unit mass variation from the measured changes in mass due to moisture absorption or desorption of the adhesive film.

In yet another embodiment, a method for determining CME values for materials includes placing one or more coupons in a gaseous environment with a target relative humidity. The one or more coupons include a flat substrate and a film of a material to be tested. The method also includes saturating or drying the one or more coupons in the gaseous environment, measuring changes in curvature of the film over time using a laser interferometer, measuring changes in mass of the film over time during the saturating or drying, converting the changes in curvature in the measurements that occur out-of-plane with a uniform radius of curvature to a strain value, and correlating the measured changes in mass to the strain values as a function of time. The method further includes determining the CME using the strain values as a fractional change in the strain value per unit mass variation from the measured changes in mass due to moisture absorption or desorption of the film. Additionally, the method includes measuring the CME for a plurality of additional coupons subjected to different curing temperatures using the process above and determining a best CME among the one or more coupons and the plurality of additional coupons.

BRIEF DESCRIPTION OF THE DRAWINGS

In order that the advantages of certain embodiments of the invention will be readily understood, a more particular description of the invention briefly described above will be rendered by reference to specific embodiments that are illustrated in the appended drawings. While it should be understood that these drawings depict only typical embodiments of the invention and are not therefore to be considered to be limiting of its scope, the invention will be described and explained with additional specificity and detail through the use of the accompanying drawings, in which:

FIG. 2 illustrates a replication process for preparing a sample adhesive on a glass substrate, according to an embodiment of the present invention.

FIG. 3A illustrates computer-generated raw images and subtracted images of an adhesive sample of a UV cured resin over time, according to an embodiment of the present invention.

FIG. 5B is a graph illustrating moisture content over the square root of time for the adhesive sample from the sample measurements, according to an embodiment of the present invention.

Unless otherwise indicated, similar reference characters denote corresponding features consistently throughout the attached drawings.

DETAILED DESCRIPTION OF THE EMBODIMENTS

Figure 1:
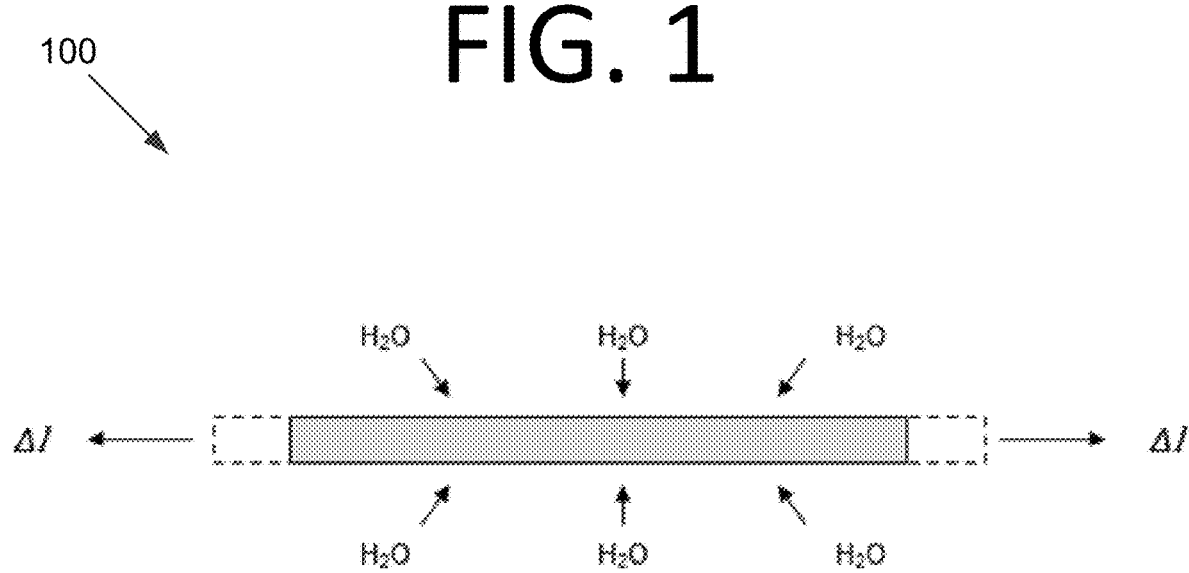
FIG. 1 illustrates the change in length in a hypothetical sample as water is absorbed.

Some embodiments of the present invention pertain to innovative and agile technique to measure accurate CME values of materials (e.g., various types of adhesives, such a resins, epoxies, etc.) in a fraction of the time (e.g., hours versus months) and with significantly smaller sample sizes (e.g., less than one gram versus more than 100 grams) compared to conventional techniques. Uncured adhesives to be tested may be in various forms, such as pre-mixed, frozen, provided in syringes, sold as stand-alone sheets, etc. In the process of some embodiments, very thin films of the material to be tested are replicated on very thin substrates, such as a silicon wafer or borosilicate glass. The film is perfectly formed on the substrate by a replication process as shown in FIG. 2.

In some embodiments, a process is utilized by which an adhesive is cured and adhered to a substrate and the surface is replicated utilizing a high-quality glass mandrel (i.e., master). For instance, in certain embodiments, the process described in U.S. Pat. No. 10,562,209 may be employed. Replication is the process of transferring the surface of a master to one or more copies of the surface. The glass master has the requisite surface flatness/roughness to employ laser interferometry in the manner described below. To prevent the adhesive from bonding to the glass master, the glass master should be coated in mold release. Also, to prevent degradation in optical quality of the adhesive surface from that of the glass master, which is important for interferometry, the mold release should be molecularly uniform.

FIG. 2, which illustrates a replication process 200 for preparing a sample adhesive on a glass substrate 206, according to an embodiment of the present invention. In order to obtain a high-quality surface finish, which is critical to the measurement process in some embodiments, a specific self-assembled monolayer mold release (e.g., perfluorinated compounds, such as perfluoroethers) is applied to a mandrel 202 to assure near perfect transfer of the mandrel topology without adherence. A replicating adhesive 204 is pressed against glass substrate 206 (e.g., a silicon wafer or borosilicate glass) using mandrel 202. Replicating adhesive 204 is then cured in place while sandwiched between mandrel 202 and glass substrate 206. This curing may be performed at room temperature or heated to simulate a processing cure, depending on how they type of adhesive used for replicating adhesive 204 is cured. Drying is then performed after curing. Mandrel 202 is then removed, leaving a thin and uniform layer of adhesive film 208 adhered to the surface of glass substrate 206. Adhesive film 208 and glass substrate 206 collectively form a sandwich stack "coupon" that is then ready to be used for CME testing. Coupon 210 exhibits relatively uniform film thickness, high surface flatness (e.g., less than 200 nanometers (nm)) and low surface roughness, which are important to measure distortion using laser interferometry.

In some embodiments, other materials that absorb moisture besides adhesives may be measured. For instance, polytetrafluoroethylene (PTFE), thermoplastics (e.g., polyethylene), etc. could be melted on the surface of the substrate instead of cured. To provide small and uniform amounts of melted material, the material may be melted between the substrate and glass master, but the surface of the substrate would be roughened or etched to ensure bonding through mechanical interlocking.

During testing, a coupon prepared in the manner described above, for example, is then placed in an environment with a desired humidity (i.e., between 0% and 100%) and saturated or dried, depending on the humidity that is used. Due to the very thin cross section of the polymer film of some embodiments (e.g., 25-75 micrometers (μm)), the saturation is typically complete within 24 hours or less. This is much thinner than the film thickness used in conventional techniques, which are typically approximately 2 millimeters (mm)—indeed, three orders of magnitude thinner. However, the saturation time depends on the specific properties of the polymer. The specimen is then analyzed utilizing a laser interferometer (e.g., a Fizeau interferometer). More specifically, the sample is measured with the laser interferometer over time when placed in the controlled humidity environment as in-situ measurements. A Fizeau interferometer includes two reflecting surfaces that are placed facing each other.

However, rather than measuring linear dimensional changes, changes in curvature over time are measured. The differences in expansion between the adhesive that absorbs/desorbs water and the glass substrate that does not absorb/desorb water creates stresses at the interface of the substrate, which result in accurate, readily measured changes in curvature of the beam of the laser interferometer. This test can both be performed as a function of weight gain or weight loss. Differences in expansion between the adhesive and the glass substrate with moisture absorption/desorption creates stresses at the interface of the substrate that are measured for changes in curvature by the laser interferometer with ~1 nm accuracy. These changes in dimensional resolution have an order of magnitude that is approximately two times higher than that of typical LVDT measurements performed using existing techniques.

Figure 3B:
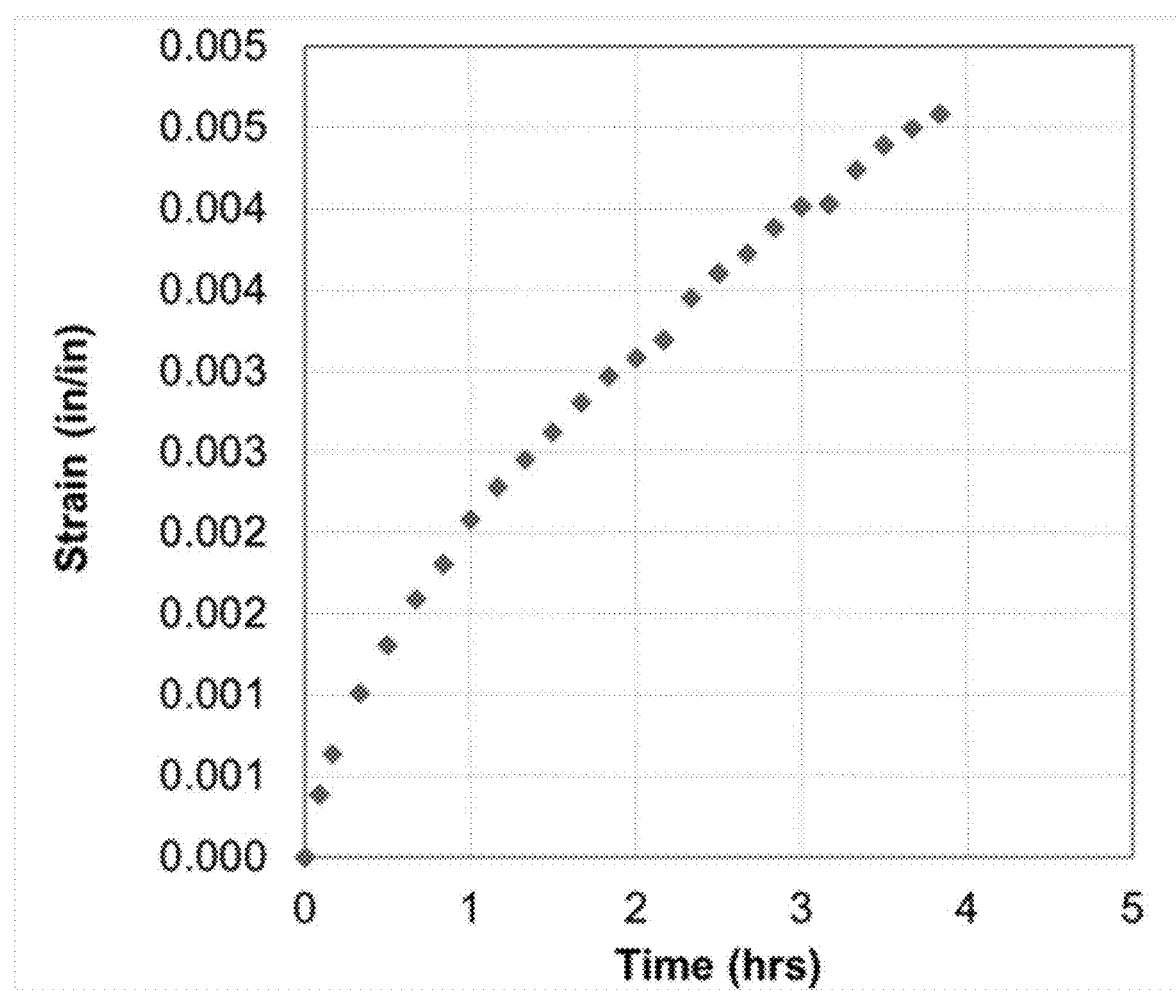
FIG. 3B is a graph illustrating measured values of strain over time for an adhesive sample of Loctite® 9394 with a 60° C. cure, according to an embodiment of the present invention.
Figure 3C:
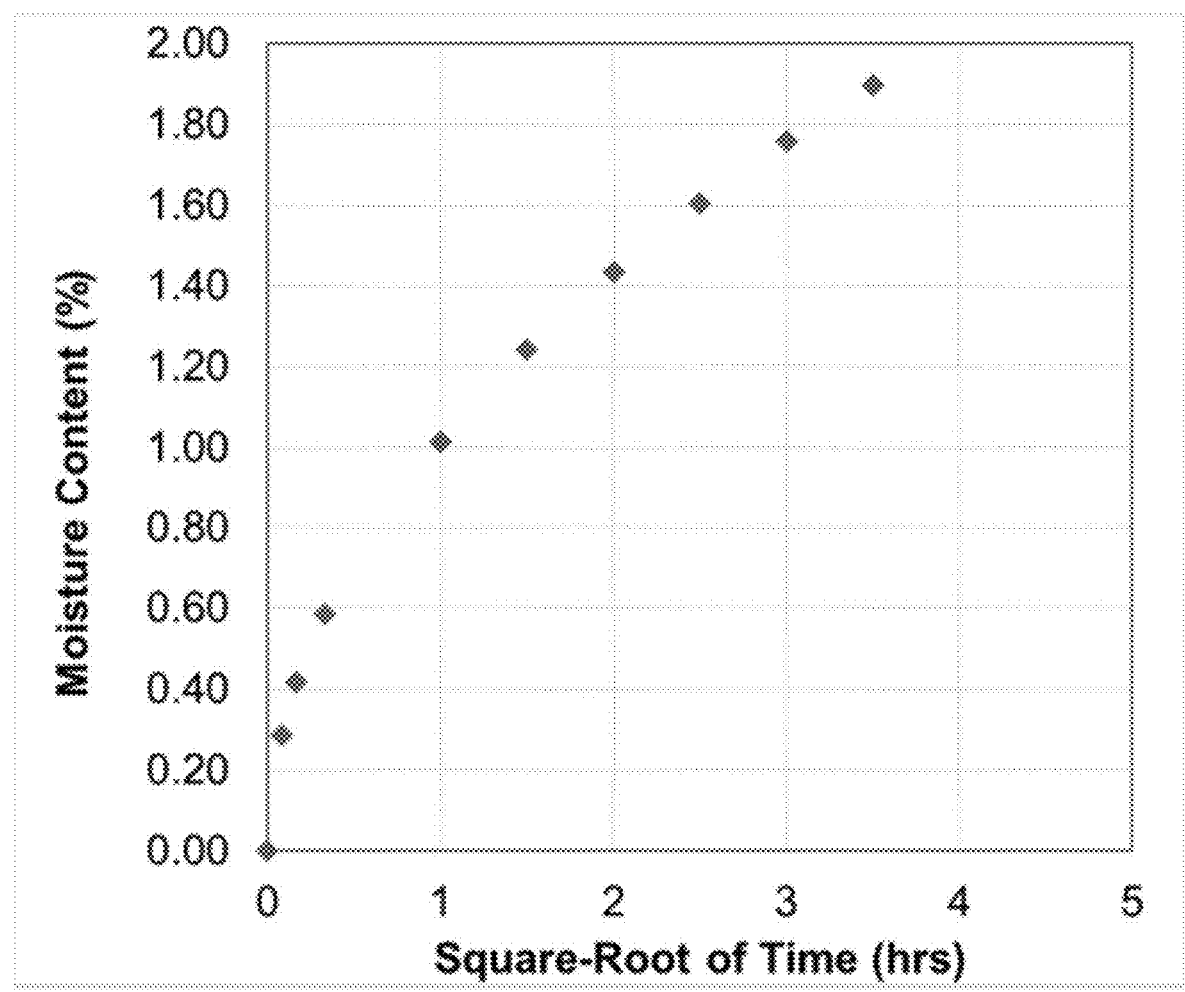
FIG. 3C is a graph illustrating measured values of moisture content over the square root of time for the same adhesive sample as FIG. 3B, according to an embodiment of the present invention.
Figure 3D:
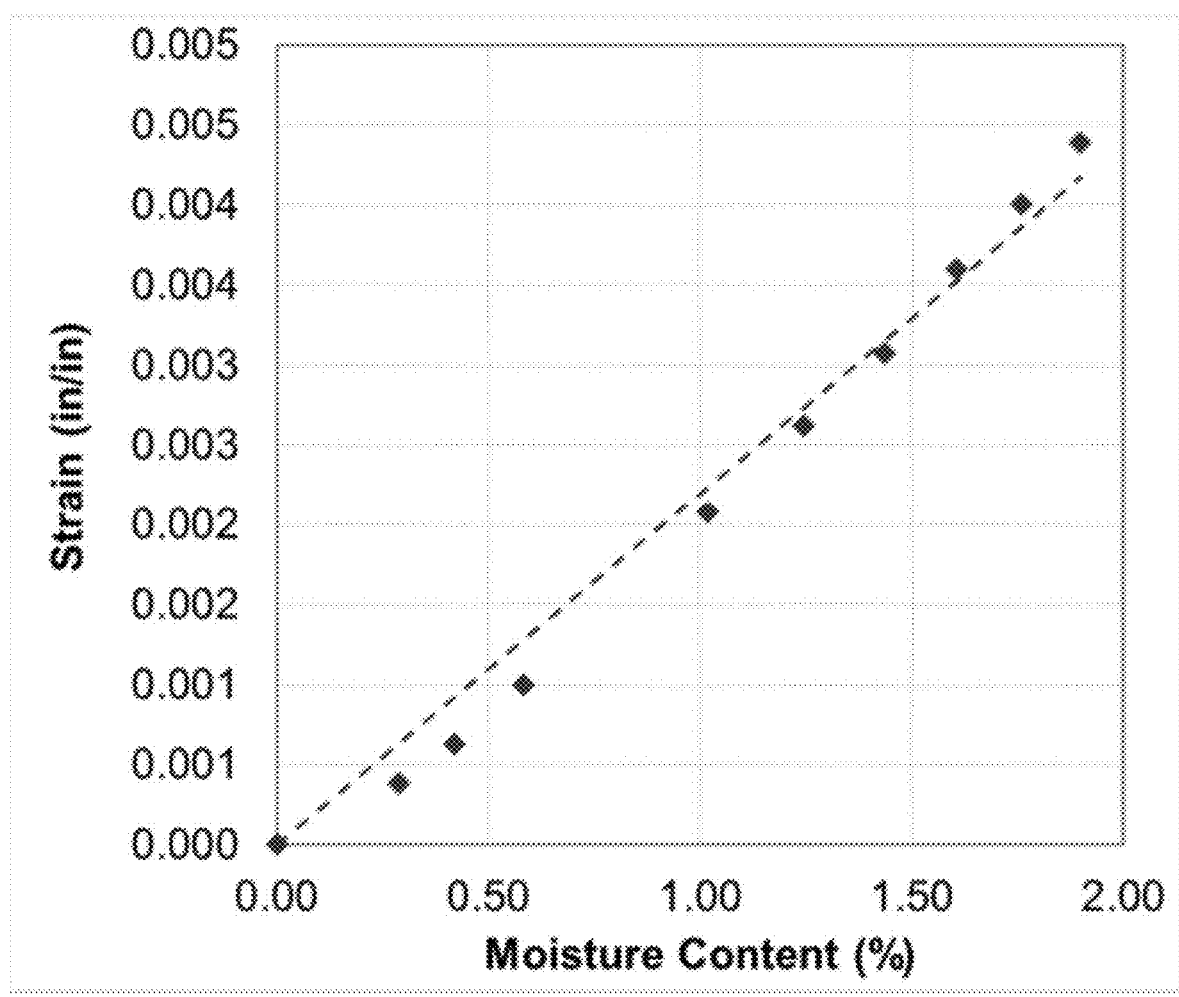
FIG. 3D is a graph illustrating measured values of strain versus moisture content for the same adhesive sample as FIG. 3B, according to an embodiment of the present invention.

A sample of Loctite® 9394 prepared using the above-described process with a 60° C. cure was tested. The adhesive samples have an inherent shape after curing onto the glass substrate. Changes with moisture absorption are not immediately apparent by monitoring raw images, such as raw images 300 of FIG. 3A. Distortion due solely to hygroscopic changes can be isolated by subtracting the initial surface from each subsequent image to produce a pixel-by-pixel topographic map of the changes, such as subtracted images 310 of FIG. 3A, which was for a UV cured resin. Graphs 320, 330, 340 of FIGS. 3B, 3C, and 3D show measured values of strain over time, moisture content over the square root of time, and strain versus moisture content, respectively, for an adhesive sample of Loctite® 9394 with a 60° C. cure. Since films are constrained by the glass substrate as bonded structures, changes in the moisture content drive out-of-plane distortion, and deformation occurs out-of-plane with a uniform radius of curvature that is converted to a strain value ε via Stoney's equation:

$$\varepsilon = \frac{\sigma}{E_f} = \frac{E_s t_s^2}{6 R t_f E_f} \quad (2)$$

where σ is the surface stress generated, E is the biaxial modulus, t is the thickness, R is the radius of curvature, f refers to the film material properties, and s refers to the substrate material properties. The strain change should still be correlated with the moisture change.

As discussed above, laser interferometry is used to measure distortion with moisture content changes in some embodiments. To calculate CME, the amount of moisture causing dimensional changes should be known. Accordingly, separate neat (i.e., standalone) adhesive coupons can be created to calculate diffusion coefficients.

Neat adhesive coupons are manufactured with an infinite thin film configuration. "Infinite thin film" refers to a configuration where diffusion can be estimated to only occur on two sides of a sample. This is a scenario where a relatively large thin film is used such that diffusion through the face is so much larger than diffusion through the edges that the effects of diffusion through the face can be ignored. These coupons are dried under nitrogen or some other suitable gas environment, such as inert gases, until the mass stabilizes. After drying, the coupons are exposed to an atmospheric air environment with a desired relative humidity (e.g., 100%, 99%, 75%, 25%, 10%, 0%, etc.) and the mass changes are monitored as a function of time.

Figure 4:
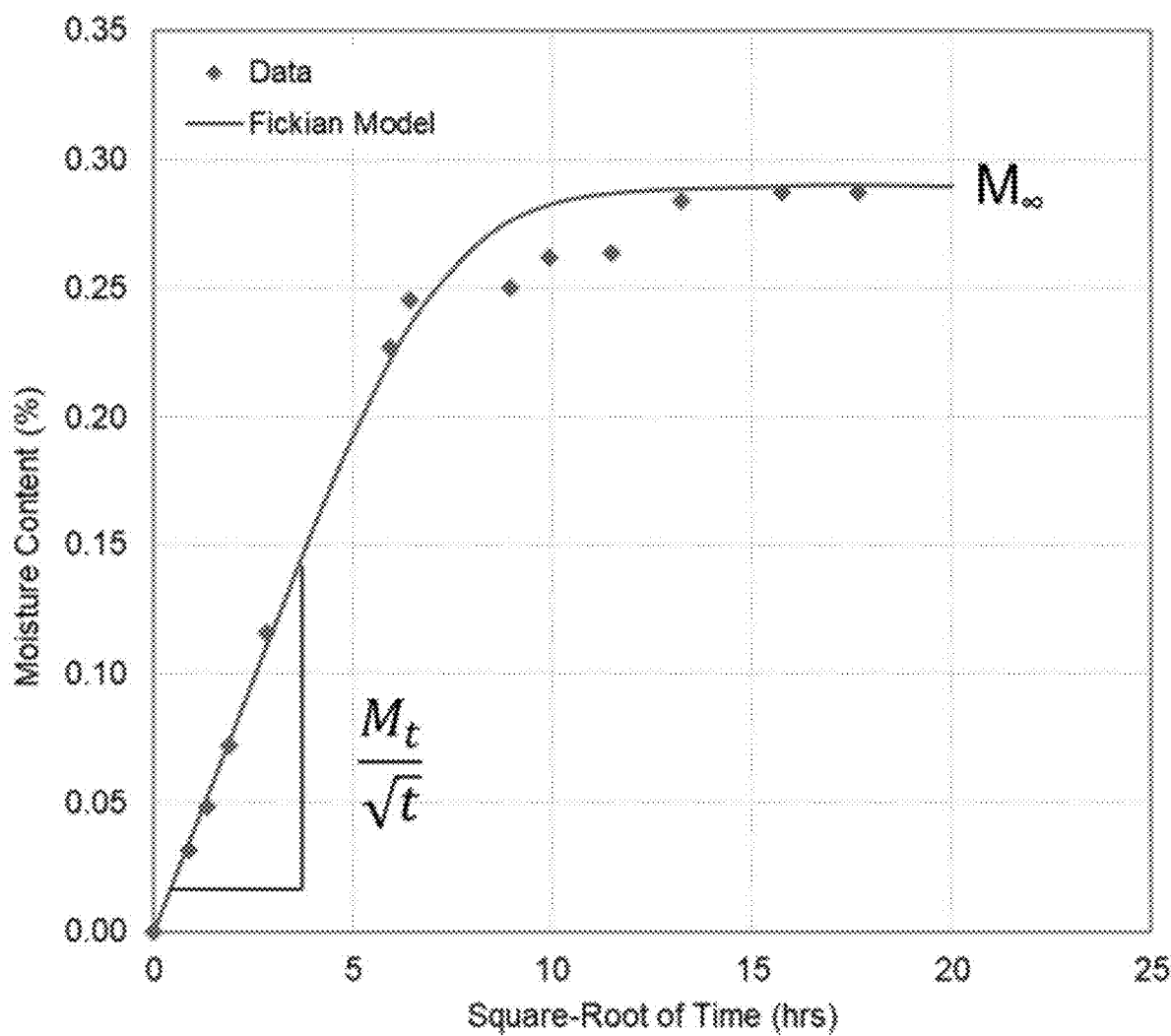
FIG. 4 is a graph illustrating a Fickian model using hypothetical data of moisture content (%) versus the square root of time.

Ideal moisture transport in polymers follows Fick's $2^{nd}$ Law of diffusion. When the moisture content is plotted versus the square root of time, the diffusion coefficient D and saturated moisture content can be extrapolated using equations (3) and (4) below, respectively.

$$D = \frac{\pi l^2}{16 M_\infty^2} \left(\frac{M_t}{\sqrt{t}}\right)^2 \quad (3)$$

$$\frac{M_t}{M_\infty} = 1 - \frac{8}{\pi^2} \sum_{n=0}^{\infty} \frac{1}{(2n+1)^2} \exp\left(\frac{-D(2n+1)^2 \pi^2}{4l^2} t\right) \quad (4)$$

where l is thickness (since the "length" of interest is the thickness of the film in this case), $M_t$ is the moisture content at a given time t, $M_\infty$ is the moisture content if diffusion were to occur over infinite time, and n is the summation integer. A graph of a Fickian model using hypothetical data of moisture content (%) versus the square root of time is shown in graph 400 of FIG. 4.

After the diffusion coefficient and saturated moisture content are evaluated, Fick's $2^{nd}$ Law can be applied for the replication geometry (infinite thin film, one face exposed) and the moisture content can be calculated and correlated against the strain at each point in time.

After correlating mass change and strain change as a function of time, CME measurements measured by the new technique of an embodiment of the present invention agree highly with conventional measurements obtained via PMIC™, having less than 5% error. Sample-to-sample error using conventional testing is also ~5%. The measured CME values for Loctite® 9394 with a 60° C. cure and Eccobond® FP4651 are shown in Table 1 below.

TABLE 1

MEASURED CME VALUES FOR TESTED ADHESIVES

| Adhesive | PMIC ™ CME (μm/m/% M) | Aerospace CME (μm/m/% M) |
| --- | --- | --- |
| Loctite ® 9394 (60° C. cure) | 2519 | 2400 |
| Eccobond ® FP4651 | 1117 | 1018 |

Figure 5A:
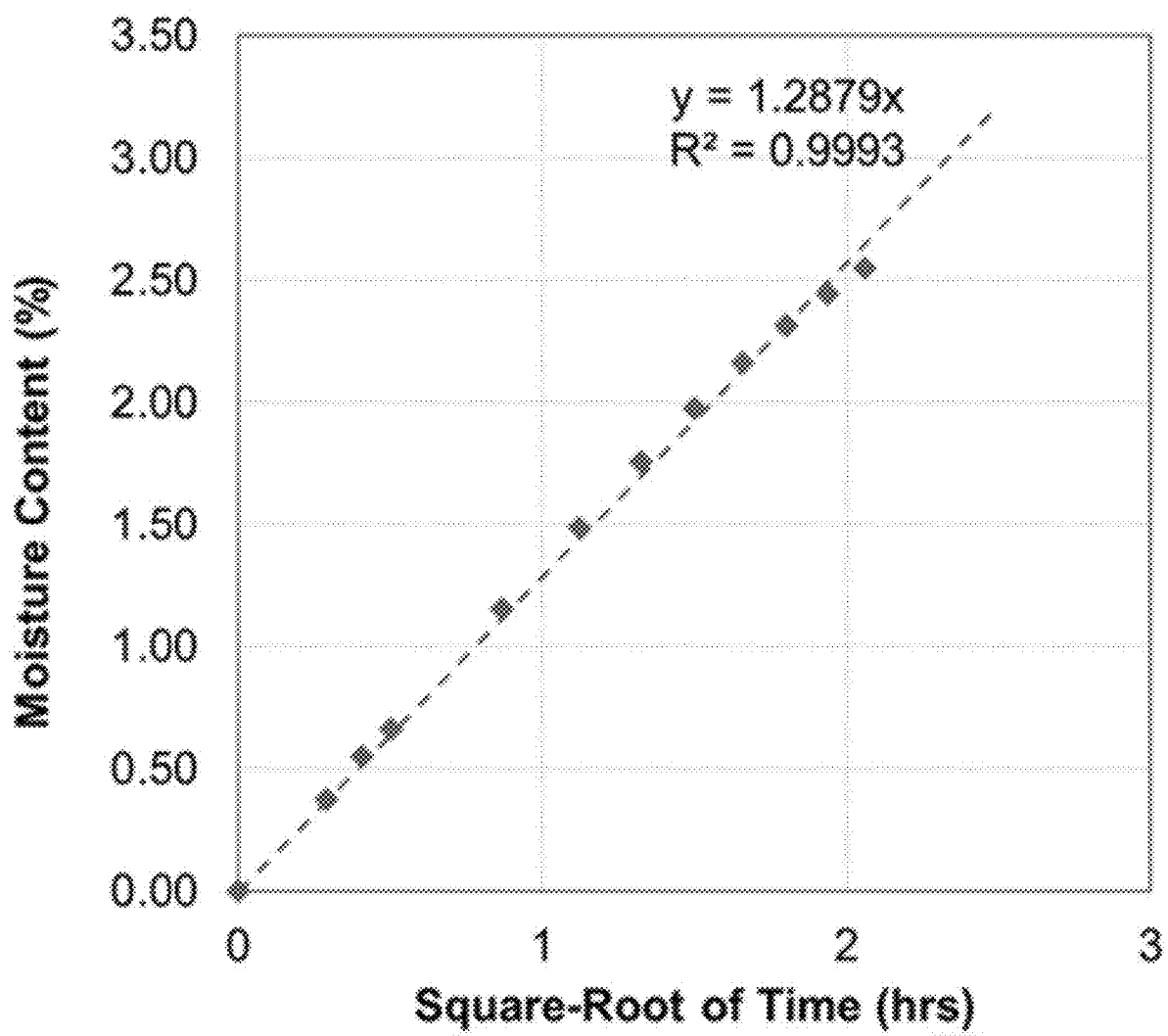
FIG. 5A is a graph illustrating strain over time for an adhesive sample of Loctite® 9394 from sample measurements, according to an embodiment of the present invention.
Figure 5C:
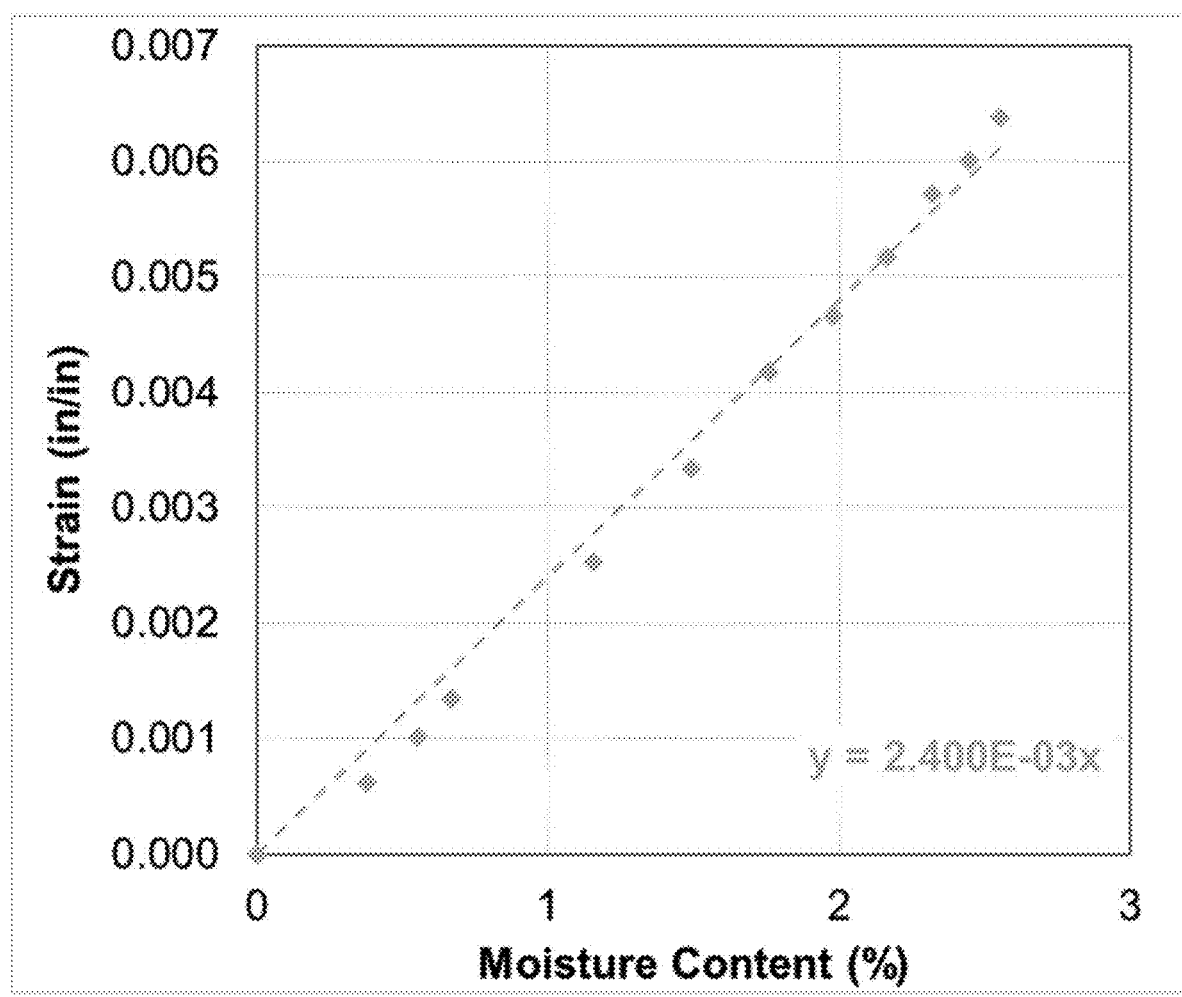
FIG. 5C is a graph illustrating strain versus moisture content for the adhesive sample from the sample measurements, according to an embodiment of the present invention.

Fit lines extrapolated from sample measurements from an adhesive sample of Loctite® 9394 for strain over time, moisture content over the square root of time, and strain versus moisture content are respectively shown in graphs 500, 510, 520 of FIGS. 5A, 5B, and 5C.

The relationship between processing and CME was also investigated. While the impact of processing on other material properties (e.g., glass transition temperature (Tg), CTE, etc.) are often investigated, CME typically is not. The elevated temperature stabilization prior to conventional testing changes the adhesive cure state.

Figure 6A:
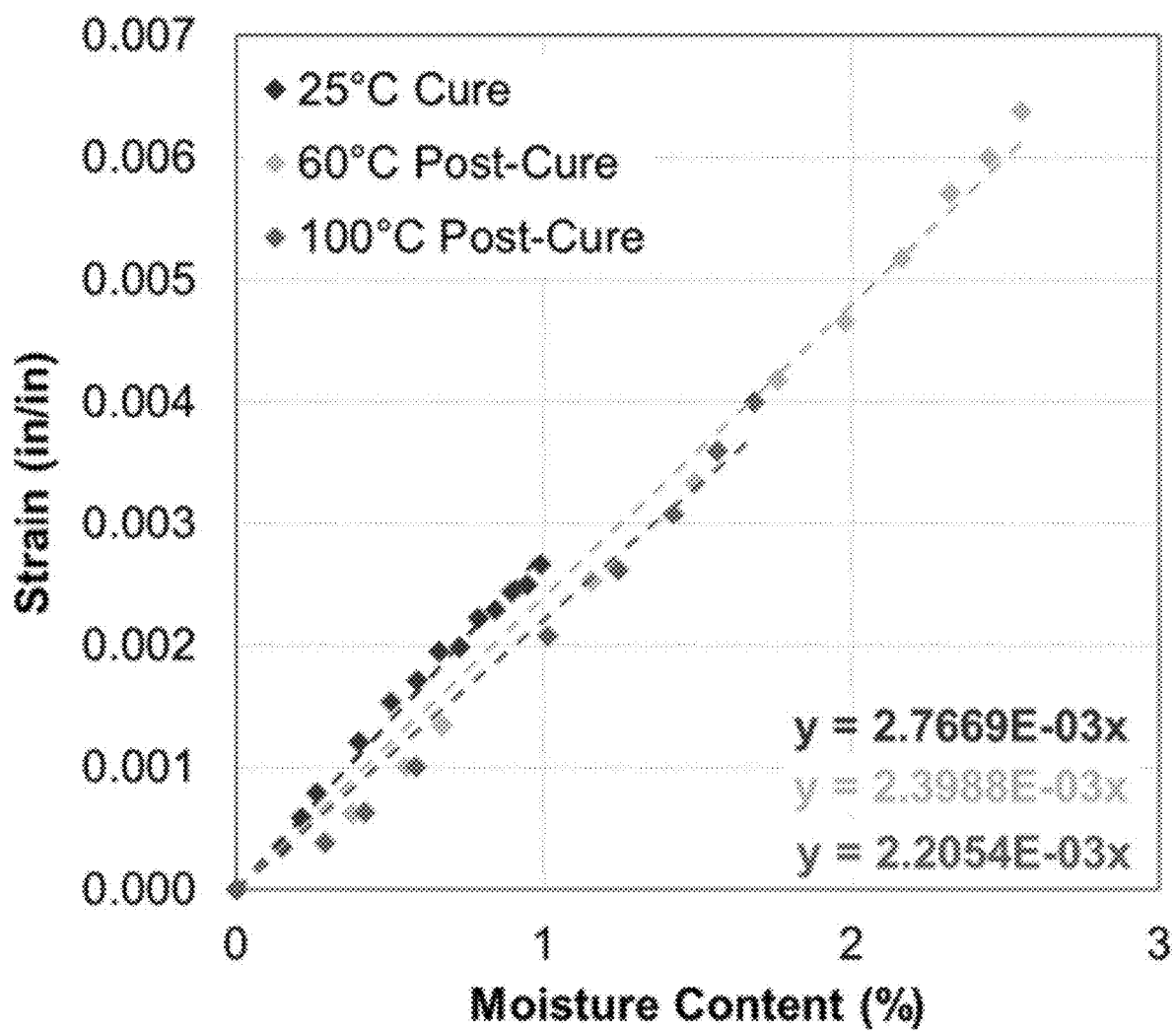
FIG. 6A is a graph illustrating strain versus moisture content for three cure states, according to an embodiment of the present invention.
Figure 6B:
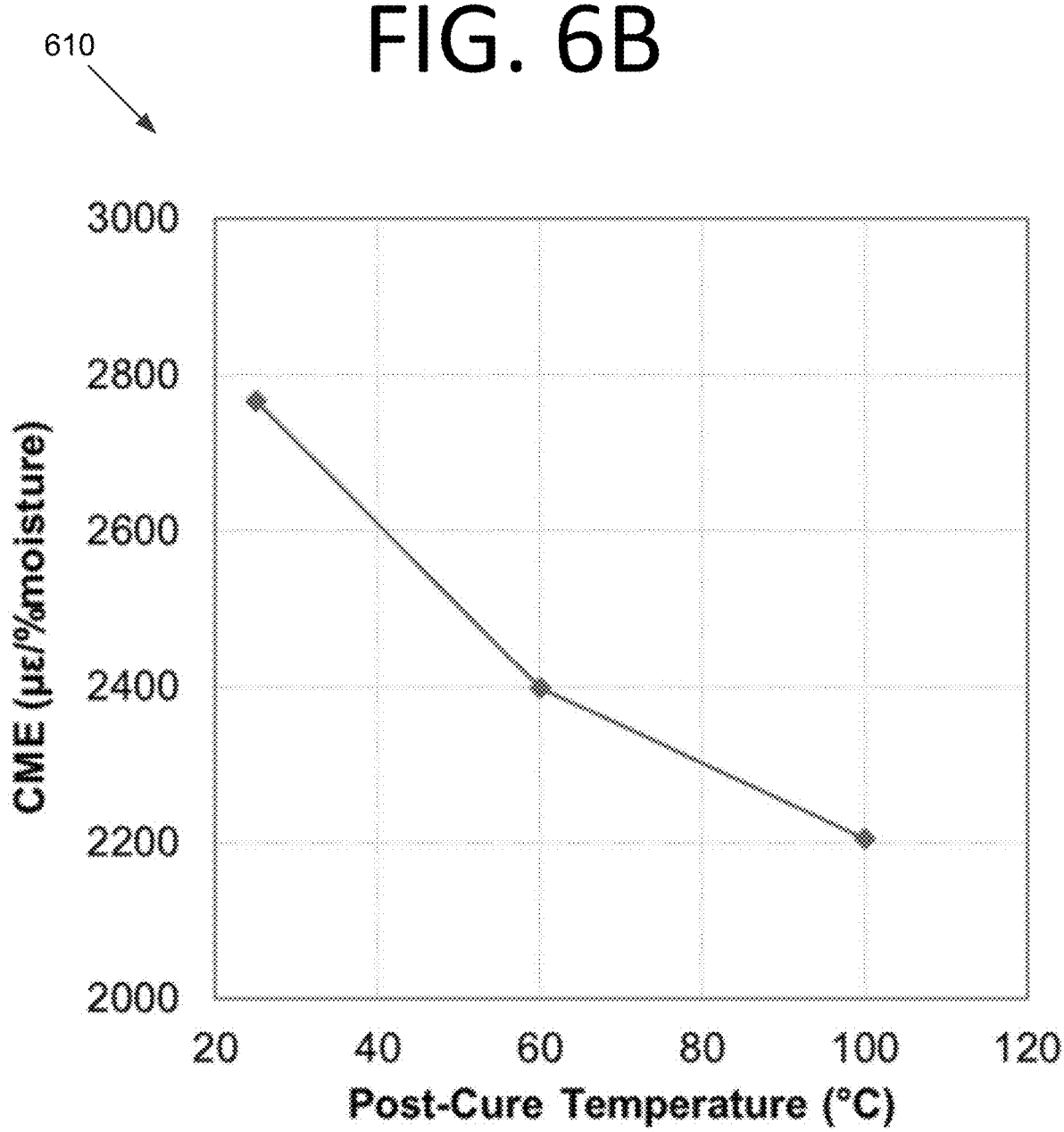
FIG. 6B is a graph illustrating CME versus post-sure temperature for Loctite® 9394, according to an embodiment of the present invention.

Strain versus moisture content for three cure states for Loctite® 9394 is shown in graph 600 of FIG. 6A, according to an embodiment of the present invention. As can be seen, a 100° C. post-cure has the lowest strain at the tested moisture contents. CME versus post-sure temperature for Loctite® 9394 is shown in graph 610 of FIG. 6B. With conventional testing, if room temperature (RT) CME is desired, pre-stabilization at 60° C. would increase cure state and CME results to 15% lower than what they are in reality. This is because if a sample is cured at RT and then stabilized at 60° C., the sample is essentially post-cured to 60° C. The measured CME measured would be 2400 parts per million (ppm) because that is the CME of the material after curing to 60° C. However, if the sample is only cured at RT and never exposed to the 60° C. temperature, the CME of the actual application material would be 2767 ppm, which is 15% larger than the measured 2400 ppm.

The new technique of some embodiments allows parametric CME studies because film is thin and can stabilize quickly at room temperature. The impact of cure temperature on CME of Loctite® 9394 was quantified in less than one week, for example. The impact of cure temperature on CME for other adhesives can also be obtained quickly using such a technique.

The technique of some embodiments also enables CME characterization of materials for which CME otherwise cannot be measured. For instance, CME for microelectronic adhesives and ultraviolet (UV) cured adhesives typically cannot be measured conventionally. Microelectronic devices commonly undergo failure due to moisture expansion/shrinking stresses, so CME is a critical parameter. However, adhesives for microelectronics are often sold for hundreds of dollars for a one cubic centimeter syringe. This makes conventional testing sample sizes prohibitively expensive (e.g., more than $5,000 in material cost alone). UV cured adhesives experience depth of penetration issues where the cure state changes through the thickness when reaching conventional sample sizes. However, using the technique of some embodiments, the thin film on the coupon does not experience penetration issues due to surface darkening, for example. Indeed, the small mass and thin film of the adhesives allow measurement of microelectronic and UV cured adhesives.

Figure 7A:
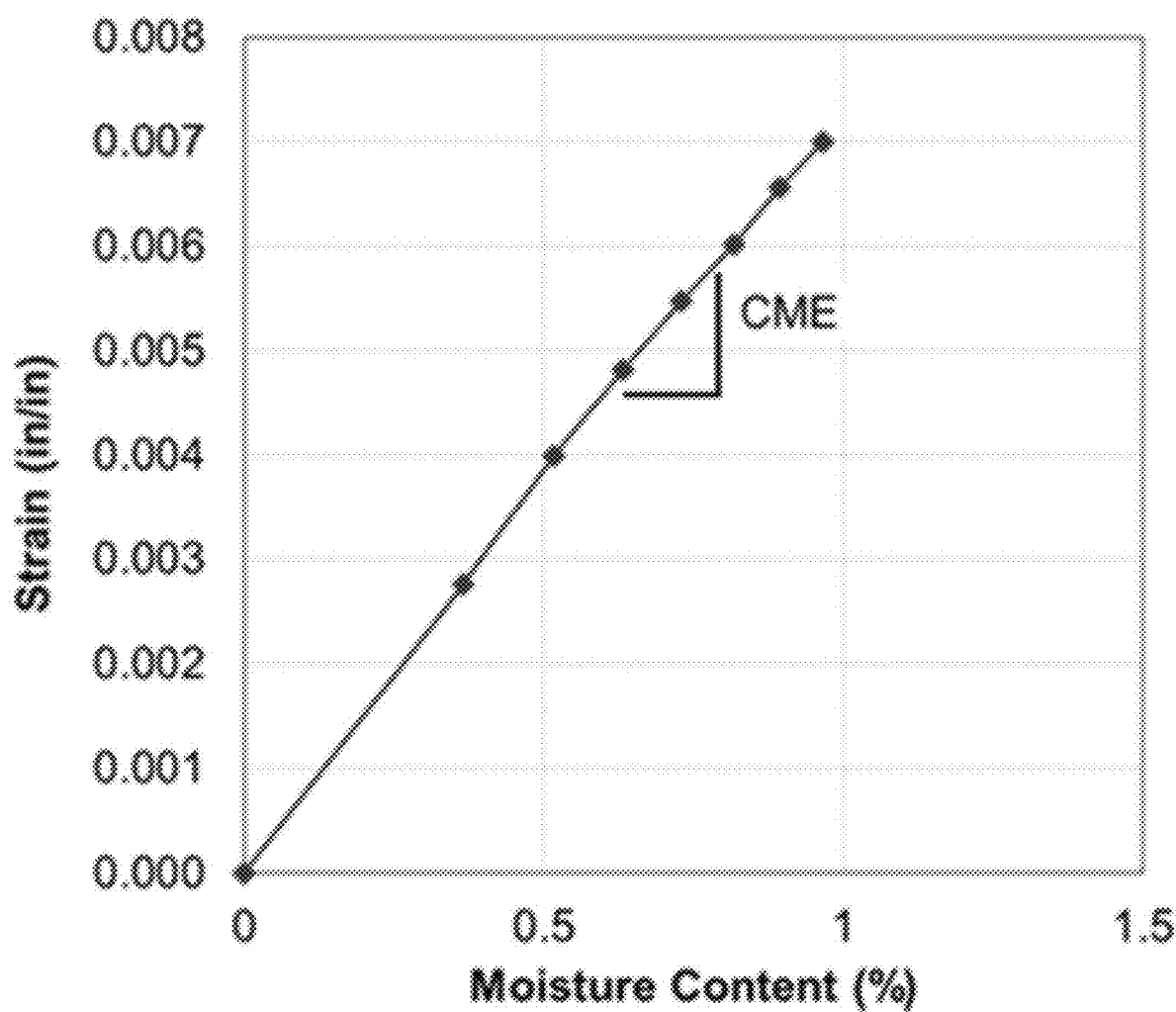
FIG. 7A is a graph illustrating strain versus moisture content for a sample of UV cured epoxy, according to an embodiment of the present invention.
Figure 7B:
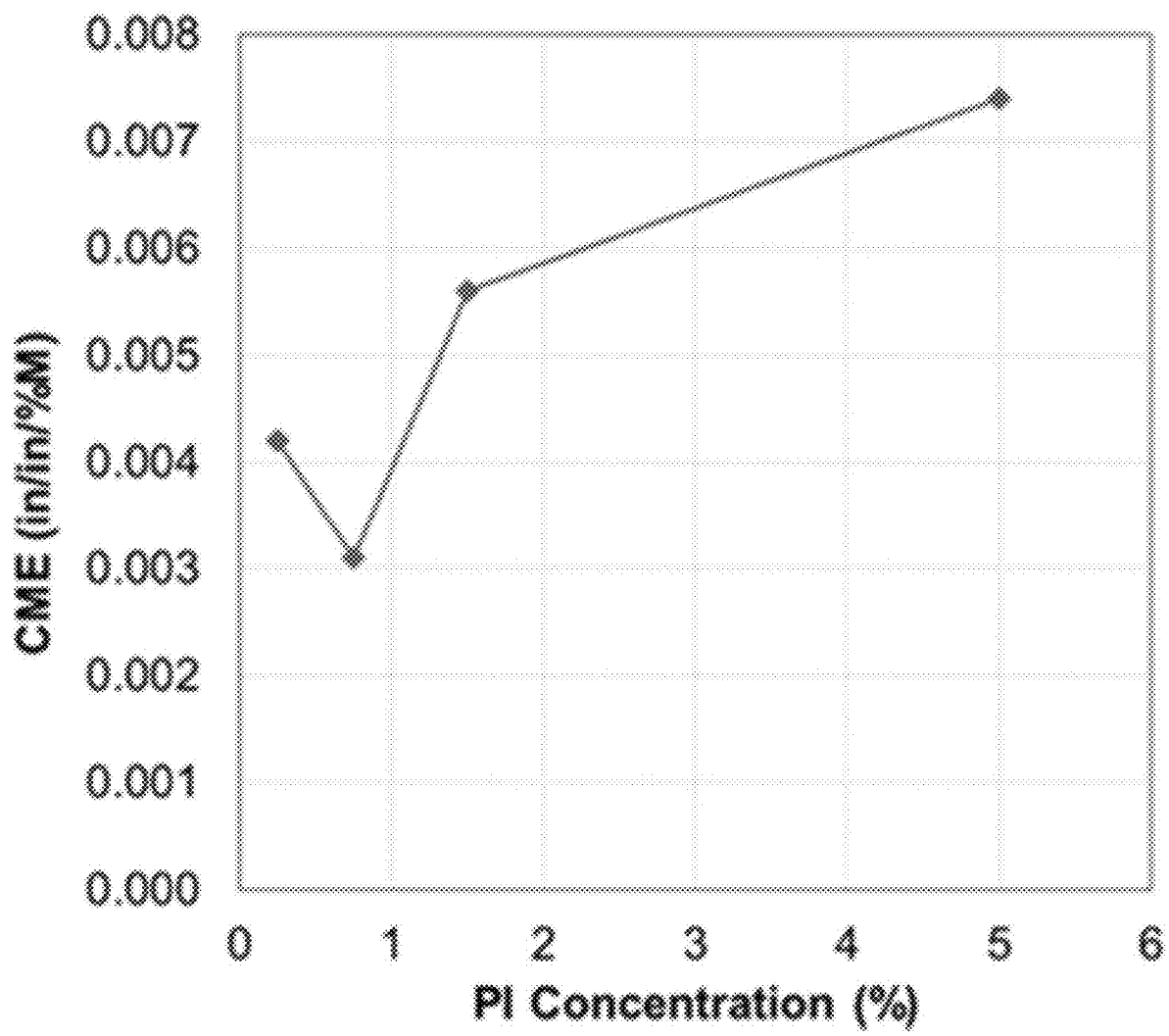
FIG. 7B is a graph illustrating CME versus PI concentration for the sample of UV cured epoxy, according to an embodiment of the present invention.

FIGS. 7A and 7B are graphs 700, 710 illustrating strain versus moisture content and CME versus photoinitiator (PI) concentration, respectively, for a sample of UV cured epoxy. PI is the material that interacts with UV light. The catalyst concentration is varied by varying the PI.

Figure 8:
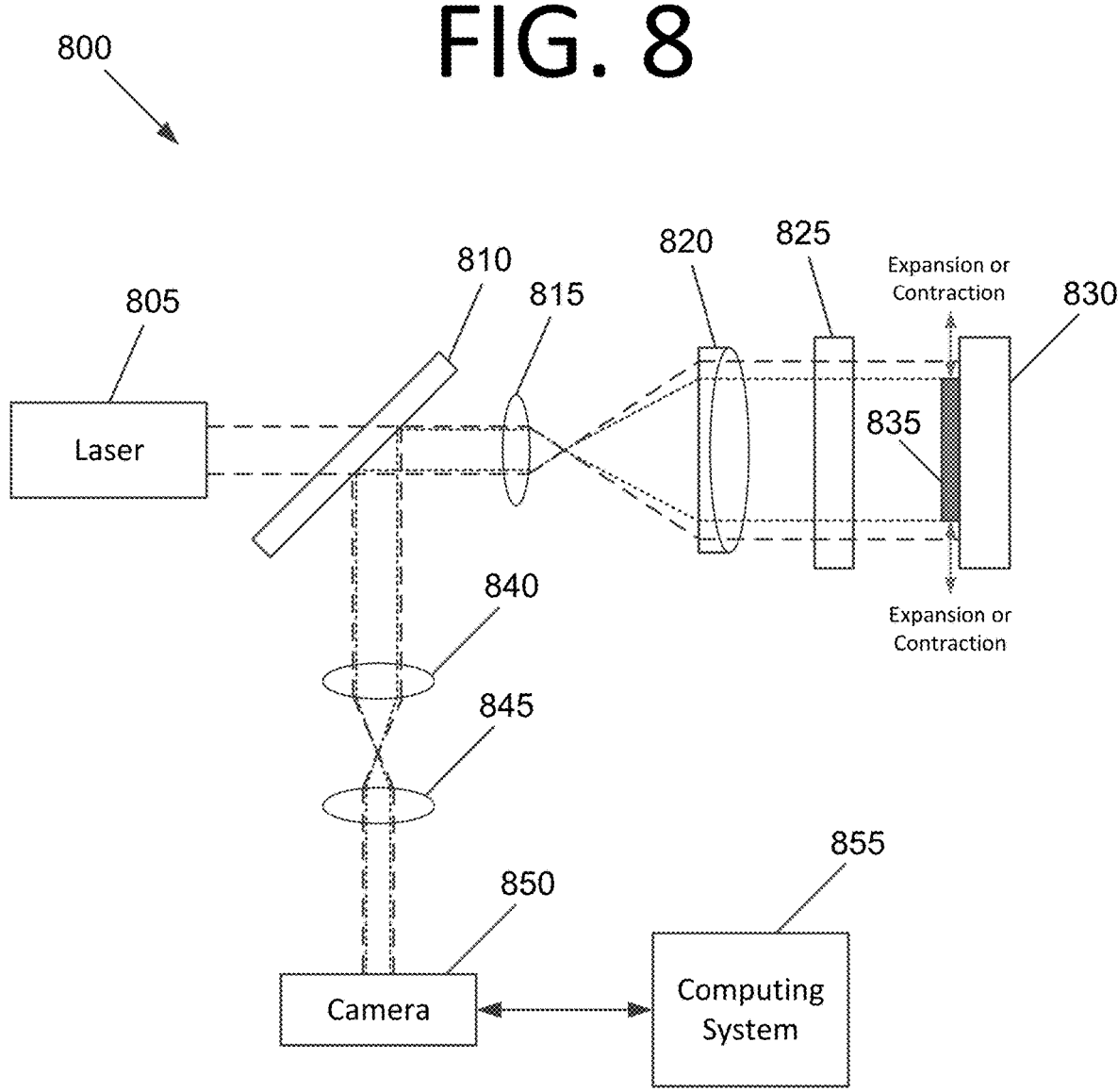
FIG. 8 is an architectural diagram illustrating a laser interferometer system configured to measure changes in curvature of a laser beam for a sample, according to an embodiment of the present invention.

FIG. 8 is an architectural diagram illustrating a Fizeau laser interferometer system 800 configured to measure changes in curvature of a laser beam for a sample, according to an embodiment of the present invention. A laser 805 sends a laser beam through a beam splitter 810. The laser beam then travels through a lens 815 that widens the laser beam and passes through another lens 820 that straightens the widened beam. This widened beam then passes through a reference 825 (e.g., transparent glass) before some of this light reflects off of substrate 830 and material sample 835, which has been prepared in accordance with the process described above.

Light reflected off of substrate 830 and sample 835 passes back through reference 825, lens 820, and lens 815 before being directed to another lens 840 by beam splitter 810. The light is then focused by a lens 845 onto a camera 850, which sends detected images to a computing system 855 (e.g., computing system 1000 of FIG. 10). It should be noted that the dashed lines denote the edges of the laser light, and portions between the dashed lines also include laser light, with the larger dashes being the original wavelength from laser 810 and the smaller dotted lines being the light reflected off sample 835. Computing system 855 generates subtracted images from the original image and determines the CME in accordance with the processes disclosed herein. However, in some embodiments, electronics of camera 850 may perform the functions of computing system 850.

Figure 9:
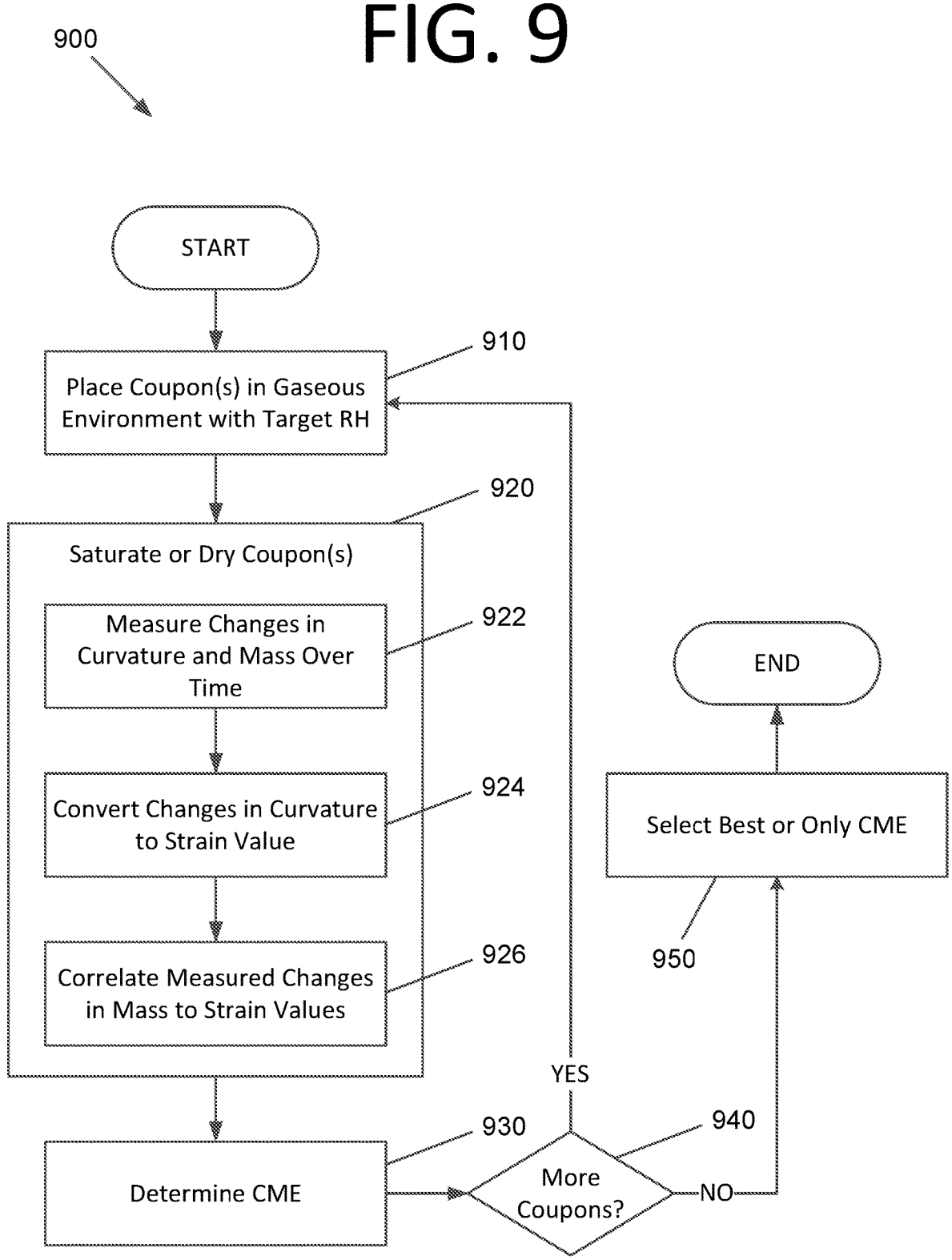
FIG. 9 is a flowchart illustrating a process for measuring the CME of an adhesive, according to an embodiment of the present invention.

FIG. 9 is a flowchart illustrating a process 900 for measuring the CME of an adhesive, according to an embodiment of the present invention. The process begins with placing one or more coupons in a gaseous environment with a target relative humidity at 910. The coupon(s) include a flat substrate and a film of the material to be tested. In some embodiments, less than 1 g of material is used. In certain embodiments, the coupon(s) have a film thickness with a uniformity of 200 nm or less, a surface flatness of less than 200 nm, and a surface roughness of 25 nm or less. In some embodiments, a cross section of the film is 25 to 75 nm. In certain embodiments, the film is an adhesive film. In some embodiments, the adhesive is a microelectronic adhesive or an ultraviolet (UV) cured adhesive.

The coupon(s) are then saturated or dried in the gaseous environment at 920, depending on the humidity. During the saturation or drying at 920, which may occur over the course of hours (e.g., 24 hours or less in some embodiments), changes in curvature and mass of the film are measured over time using a laser interferometer at 922 and the changes in curvature in the measurements that occur out-of-plane with a uniform radius of curvature are converted to a strain value 924. In some embodiments, the changes in the curvature of the film and changes in height of each pixel are determined by subtracting an initial surface image from an image at a given time, producing a subtracted image. In certain embodiments, the subtracted image includes a pixel-by-pixel topographic map of the changes in the curvature of the film. In some embodiments, the measured changes in mass are correlated to the strain values as a function of time at 926.

In certain embodiments, the changes in mass and strain values are measured simultaneously. For instance, CME measurements may be performed two ways in some embodiments. A first way is to use one sample coupon for mass measurement and another sample coupon for strain measurement. A second way is to perform an in-situ mass measurement during strain measurements on the same sample coupon and account for the mass of the glass substrate. Both produce equivalent CME values.

The CME is then determined at 930 using the strain values as a fractional change in the strain value per unit mass variation from the measured changes in mass due to moisture desorption or absorption of the adhesive film. If there are more coupons to process at 940, the process returns to step 910 for the next coupon(s). This may be done, for instance, if different materials, different cure times, different cure temperatures, different humidities, any combination thereof, etc. are to be tested. If suitable testing facilities are available, at least some of these tests may be performed simultaneously. If only a single coupon (or multiple coupons at the same time) is to be tested or all coupons have been tested in different testing runs at 940, the best or only CME is selected at 950.

CME characterization is critical to space applications, as well as terrestrial and aircraft applications. However, there are limitations with conventional testing that prevent the widespread characterization of many materials. The technique of some embodiments facilitates accurate measurement of CME in a fraction of the time with a fraction of the material as compared to conventional testing techniques.

A replication technique is used in some embodiments to manufacture highly flat and smooth adhesive samples, moisture is introduced in a controlled humidity atmosphere, distortion is monitored with an accurate laser interferometer (e.g., —1 nm accuracy), and measurements are correlated with moisture content change. Some embodiments decrease sample size by three orders of magnitude as compared with conventional techniques. This smaller mass requirement enables measurement of expensive microelectronic adhesives that were previously cost-prohibitive to measure. Also, thinner films are used, allowing CME measurements of UV cured adhesives that would otherwise have depth of penetration issues. Furthermore, saturation occurs quickly, allowing pre-stabilization at room temperature, which enabled parametric studies as a function of processing or cure state. Additionally, testing occurs within hours versus months, enabling short lead times for root-cause investigations. Yet another advantage occurs for adhesives that have relatively high cure temperatures (e.g., 150° C. or more), for example. Placing conventional sample sizes of such adhesives in an oven would cause CTE mismatches and buckling, which does not occur in some embodiments.

Figure 10:
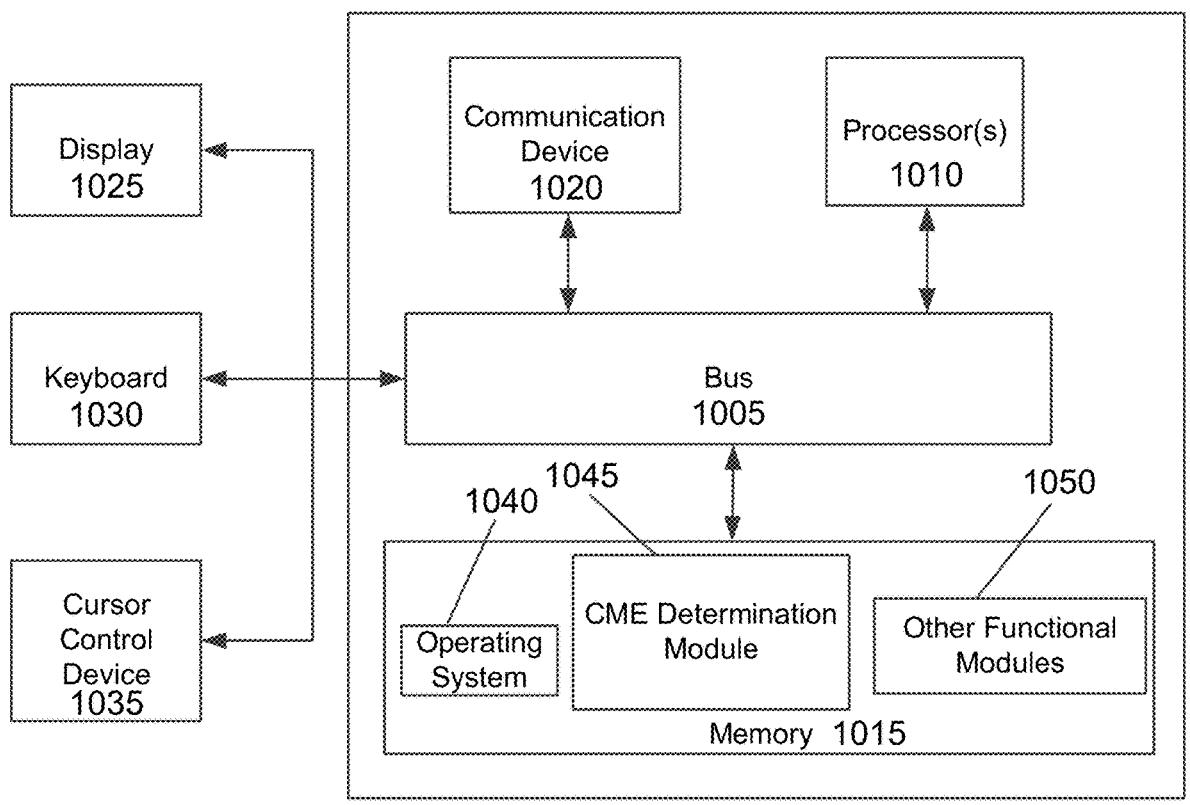
FIG. 10 is an architectural diagram illustrating a computing system 1000 configured to perform CME detection, according to an embodiment of the present invention.

FIG. 10 is an architectural diagram illustrating a computing system 1000 configured to perform CME detection, according to an embodiment of the present invention. In some embodiments, computing system 1000 may be one or more of the computing systems depicted and/or described herein. Computing system 1000 includes a bus 1005 or other communication mechanism for communicating information, and processor(s) 1010 coupled to bus 1005 for processing information. Processor(s) 1010 may be any type of general or specific purpose processor, including a Central Processing Unit (CPU), an Application Specific Integrated Circuit (ASIC), a Field Programmable Gate Array (FPGA), a Graphics Processing Unit (GPU), multiple instances thereof, and/or any combination thereof. Processor(s) 1010 may also have multiple processing cores, and at least some of the cores may be configured to perform specific functions. Multi-parallel processing may be used in some embodiments. In certain embodiments, at least one of processor(s) 1010 may be a neuromorphic circuit that includes processing elements that mimic biological neurons. In some embodiments, neuromorphic circuits may not require the typical components of a Von Neumann computing architecture.

Computing system 1000 further includes a memory 1015 for storing information and instructions to be executed by processor(s) 1010. Memory 1015 can be comprised of any combination of Random Access Memory (RAM), Read Only Memory (ROM), flash memory, cache, static storage such as a magnetic or optical disk, or any other types of non-transitory computer-readable media or combinations thereof. Non-transitory computer-readable media may be any available media that can be accessed by processor(s) 1010 and may include volatile media, non-volatile media, or both. The media may also be removable, non-removable, or both.

Additionally, computing system 1000 includes a communication device 1020, such as a transceiver, to provide access to a communications network via a wireless and/or wired connection. In some embodiments, communication device 1020 may be configured to use Frequency Division Multiple Access (FDMA), Single Carrier FDMA (SC-FDMA), Time Division Multiple Access (TDMA), Code Division Multiple Access (CDMA), Orthogonal Frequency Division Multiplexing (OFDM), Orthogonal Frequency Division Multiple Access (OFDMA), Global System for Mobile (GSM) communications, General Packet Radio Service (GPRS), Universal Mobile Telecommunications System (UMTS), cdma2000, Wideband CDMA (W-CDMA), High-Speed Downlink Packet Access (HSDPA), High-Speed Uplink Packet Access (HSUPA), High-Speed Packet Access (HSPA), Long Term Evolution (LTE), LTE Advanced (LTE-A), 802.11x, Wi-Fi, Zigbee, Ultra-WideBand (UWB), 802.16x, 802.15, Home Node-B (HnB), Bluetooth, Radio Frequency Identification (RFID), Infrared Data Association (IrDA), Near-Field Communications (NFC), fifth generation (5G), New Radio (NR), any combination thereof, and/or any other currently existing or future-implemented communications standard and/or protocol without deviating from the scope of the invention. In some embodiments, communication device 520 may include one or more antennas that are singular, arrayed, phased, switched, beamforming, beam-steering, a combination thereof, and or any other antenna configuration without deviating from the scope of the invention.

Processor(s) 1010 are further coupled via bus 1005 to a display 1025, such as a plasma display, a Liquid Crystal Display (LCD), a Light Emitting Diode (LED) display, a Field Emission Display (FED), an Organic Light Emitting Diode (OLED) display, a flexible OLED display, a flexible substrate display, a projection display, a 4K display, a high definition display, a Retina® display, an In-Plane Switching (IPS) display, or any other suitable display for displaying information to a user. Display 1025 may be configured as a touch (haptic) display, a three dimensional (3D) touch display, a multi-input touch display, a multi-touch display, etc. using resistive, capacitive, surface-acoustic wave (SAW) capacitive, infrared, optical imaging, dispersive signal technology, acoustic pulse recognition, frustrated total internal reflection, etc. Any suitable display device and haptic I/O may be used without deviating from the scope of the invention.

A keyboard 1030 and a cursor control device 1035, such as a computer mouse, a touchpad, etc., are further coupled to bus 1005 to enable a user to interface with computing system 1000. However, in certain embodiments, a physical keyboard and mouse may not be present, and the user may interact with the device solely through display 1025 and/or a touchpad (not shown). Any type and combination of input devices may be used as a matter of design choice. In certain embodiments, no physical input device and/or display is present. For instance, the user may interact with computing system 1000 remotely via another computing system in communication therewith, or computing system 1000 may operate autonomously.

Memory 1015 stores software modules that provide functionality when executed by processor(s) 1010. The modules include an operating system 1040 for computing system 1000. The modules further include a CME determination module 1045 that is configured to perform computations for the processes described herein or derivatives thereof. Computing system 1000 may include one or more additional functional modules 1050 that include additional functionality.

One skilled in the art will appreciate that a "system" could be embodied as a server, an embedded computing system, a personal computer, a console, a personal digital assistant (PDA), a cell phone, a tablet computing device, a quantum computing system, or any other suitable computing device, or combination of devices without deviating from the scope of the invention. Presenting the above-described functions as being performed by a "system" is not intended to limit the scope of the present invention in any way, but is intended to provide one example of the many embodiments of the present invention. Indeed, methods, systems, and apparatuses disclosed herein may be implemented in localized and distributed forms consistent with computing technology, including cloud computing systems. The computing system could be part of or otherwise accessible by a local area network (LAN), a mobile communications network, a satellite communications network, the Internet, a public or private cloud, a hybrid cloud, a server farm, any combination thereof, etc. Any localized or distributed architecture may be used without deviating from the scope of the invention.

It should be noted that some of the system features described in this specification have been presented as modules, in order to more particularly emphasize their implementation independence. For example, a module may be implemented as a hardware circuit comprising custom very large scale integration (VLSI) circuits or gate arrays, off-the-shelf semiconductors such as logic chips, transistors, or other discrete components. A module may also be implemented in programmable hardware devices such as field programmable gate arrays, programmable array logic, programmable logic devices, graphics processing units, or the like.

A module may also be at least partially implemented in software for execution by various types of processors. An identified unit of executable code may, for instance, include one or more physical or logical blocks of computer instructions that may, for instance, be organized as an object, procedure, or function. Nevertheless, the executables of an identified module need not be physically located together, but may include disparate instructions stored in different locations that, when joined logically together, comprise the module and achieve the stated purpose for the module. Further, modules may be stored on a computer-readable medium, which may be, for instance, a hard disk drive, flash device, RAM, tape, and/or any other such non-transitory computer-readable medium used to store data without deviating from the scope of the invention.

Indeed, a module of executable code could be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices, and may exist, at least partially, merely as electronic signals on a system or network.

It will be readily understood that the components of various embodiments of the present invention, as generally described and illustrated in the figures herein, may be arranged and designed in a wide variety of different configurations. Thus, the detailed description of the embodiments of the systems, apparatuses, methods, and computer programs of the present invention, as represented in the attached figures, is not intended to limit the scope of the invention as claimed, but is merely representative of selected embodiments of the invention.

The features, structures, or characteristics of the invention described throughout this specification may be combined in any suitable manner in one or more embodiments. For example, reference throughout this specification to "certain embodiments," "some embodiments," or similar language means that a particular feature, structure, or characteristic described in connection with the embodiment is included in at least one embodiment of the present invention. Thus, appearances of the phrases "in certain embodiments," "in some embodiment," "in other embodiments," or similar language throughout this specification do not necessarily all refer to the same group of embodiments and the described features, structures, or characteristics may be combined in any suitable manner in one or more embodiments.

It should be noted that reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussion of the features and advantages, and similar language, throughout this specification may, but do not necessarily, refer to the same embodiment.

It should be noted that reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussion of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize that the invention can be practiced without one or more of the specific features or advantages of a particular embodiment. In other instances, additional features and advantages may be recognized in certain embodiments that may not be present in all embodiments of the invention.

One having ordinary skill in the art will readily understand that the invention as discussed above may be practiced with steps in a different order, and/or with hardware elements in configurations which are different than those which are disclosed. Therefore, although the invention has been described based upon these preferred embodiments, it would be apparent to those of skill in the art that certain modifications, variations, and alternative constructions would be apparent, while remaining within the spirit and scope of the invention. In order to determine the metes and bounds of the invention, therefore, reference should be made to the appended claims.

The invention claimed is:

1. A method for determining coefficient of moisture expansion (CME) values for materials, comprising:
    placing two or more coupons in a gaseous environment with a target relative humidity, each of the two or more coupons comprising a flat substrate and a film of a material to be tested;
    saturating or drying the two or more coupons in the gaseous environment;
    during the saturating or drying, simultaneously measuring changes in curvature of the film over time using a laser interferometer and measuring changes in mass of the film over time for each coupon of the two or more coupons;
    converting the changes in curvature in the measurements that occur out-of-plane with a uniform radius of curvature to a strain value for the two or more coupons;
    determining the CME using the strain values as a fractional change in the strain value per unit mass variation from the measured changes in mass due to moisture absorption or desorption of the film for the two or more coupons; and
    selecting a [best] lowest CME value of the determined CME values [for] of the two or more coupons, wherein
    the changes in mass and strain values of the film are measured simultaneously on each coupon of the two or more coupons,
    an amount of the material in the film is less than one gram (g), and
    a test time in the gaseous environment is 24 hours or less.

2. The method of claim 1, wherein the film is an adhesive film.

3. The method of claim 1, further comprising:
    correlating the measured changes in mass to the strain values as a function of time.

4. The method of claim 1, wherein the two or more coupons have a film thickness with a uniformity of 200 nanometers (nm) or less, a surface flatness of less than 200 nm, and a surface roughness of 25 nm or less.

5. The method of claim 1, wherein a cross section of the film is 25 to 75 nanometers (nm).

6. The method of claim 1, wherein the changes in the curvature of the film and changes in height of each pixel are determined by subtracting an initial surface image from an image at a given time, producing a subtracted image.

7. The method of claim 6, wherein the subtracted image comprises a pixel-by-pixel topographic map of the changes in the curvature of the film.

8. The method of claim 1, further comprising:
    measuring the CME for a plurality of additional coupons subjected to different curing temperatures using the process of claim 1; and
    determining the lowest CME among the two or more coupons and the plurality of additional coupons.

9. The method of claim 1, wherein the film is an adhesive, the adhesive comprising a microelectronic adhesive or an ultraviolet (UV) cured adhesive.

10. A method for determining coefficient of moisture expansion (CME) values for adhesive materials, comprising:
    placing two or more coupons in a gaseous environment with a target relative humidity, each of the two or more coupons comprising a flat substrate and an adhesive film of an adhesive to be tested;
    saturating or drying the two or more coupons in the gaseous environment;
    during the saturating or drying, simultaneously measuring changes in curvature of the adhesive film over time using a laser interferometer and measuring changes in mass of the adhesive film over time for each coupon of the two or more coupons;
    converting the changes in curvature in the measurements that occur out-of-plane with a uniform radius of curvature to a strain value;
    determining the CME using the strain values as a fractional change in the strain value per unit mass variation from the measured changes in mass due to moisture absorption or desorption of the adhesive film for the two or more coupons; and
    selecting a [best] lowest CME value of the determined CME values [for] of the two or more coupons, wherein
    the changes in mass and strain values of the adhesive film are measured simultaneously on each coupon of the two or more coupons,
    an amount of the adhesive of the adhesive film is less than one gram (g), and
    a test time in the gaseous environment is 24 hours or less.

11. The method of claim 10, wherein the two or more coupons have a film thickness with a uniformity of 200 nanometers (nm) or less, a surface flatness of less than 200 nm, and a surface roughness of 25 nm or less.

12. The method of claim 10, wherein a cross section of the adhesive film is 25 to 75 nanometers (nm).

13. The method of claim 10, wherein the changes in the curvature of the adhesive film and changes in height of each pixel are determined by subtracting an initial surface image from an image at a given time, producing a subtracted image.

14. The method of claim 13, wherein the subtracted image comprises a pixel-by-pixel topographic map of the changes in the curvature of the adhesive film.

15. The method of claim 10, further comprising:
    measuring the CME for a plurality of additional coupons subjected to different curing temperatures using the process of claim 10; and
    determining the lowest CME among the two or more coupons and the plurality of additional coupons.

16. The method of claim 10, wherein the adhesive film comprises a microelectronic adhesive or an ultraviolet (UV) cured adhesive.

17. A method for determining coefficient of moisture expansion (CME) values for materials, comprising:
    placing two or more coupons in a gaseous environment with a target relative humidity, each of the two or more coupons comprising a flat substrate and a film of a material to be tested;
    saturating or drying the two or more coupons in the gaseous environment;
    during the saturating or drying, simultaneously measuring changes in curvature of the film over time using a laser interferometer and measuring changes in mass of the film over time for each coupon of the two or more coupons;
    converting the changes in curvature in the measurements that occur out-of-plane with a uniform radius of curvature to a strain value for each coupon of the two or more coupons;

correlating the measured changes in mass to the strain values as a function of time for each coupon of the two or more coupons;

determining the CME using the strain values as a fractional change in the strain value per unit mass variation from the measured changes in mass due to moisture absorption or desorption of the film for each coupon of the two or more coupons;

measuring the CME for a plurality of additional coupons subjected to different curing temperatures using the process above;

determining a [best] lowest CME among the two or more coupons and the plurality of additional coupons; and wherein the changes in mass and strain values of the film are measured simultaneously on each coupon of the two or more coupons, an amount of the material in the film is less than one gram (g), and a test time in the gaseous environment is 24 hours or less.

18. The method of claim 17, wherein the film is an adhesive film.

19. The method of claim 18, wherein the adhesive film comprises a microelectronic adhesive or an ultraviolet (UV) cured adhesive.

20. The method of claim 17, wherein an amount of material in the film is less than one gram (g).

21. The method of claim 17, wherein the two or more coupons have a film thickness with a uniformity of 200 nanometers (nm) or less, a surface flatness of less than 200 nm, and a surface roughness of 25 nm or less.

22. The method of claim 17, wherein a cross section of the film is 25 to 75 nanometers (nm).

23. The method of claim 17, wherein the changes in the curvature of the film and changes in height of each pixel are determined by subtracting an initial surface image from an image at a given time, producing a subtracted image.

24. The method of claim 23, wherein the subtracted image comprises a pixel-by-pixel topographic map of the changes in the curvature of the film.

* * * * *